United States Patent [19]

Muia et al.

[11] Patent Number: 5,015,395
[45] Date of Patent: May 14, 1991

[54] METHOD FOR CONTROLLING ZEBRA MUSSELS USING DIALKYL DIALLYL AMMONIUM POLYMERS

[75] Inventors: Ramon A. Muia, Coraopolis; Rodney M. Donlan, Bridgeville, both of Pa.

[73] Assignee: Calgon Corporation, Pittsburgh, Pa.

[21] Appl. No.: 511,156

[22] Filed: Apr. 18, 1990

[51] Int. Cl.$^5$ ............................ C02F 1/50; C02F 1/68
[52] U.S. Cl. ................................... 210/755; 210/698; 210/764; 514/642
[58] Field of Search ............... 210/755, 764, 698, 749; 514/642

[56] References Cited

U.S. PATENT DOCUMENTS

| | | | |
|---|---|---|---|
| 4,113,709 | 9/1978 | Guinlan | 210/500.1 |
| 4,462,914 | 7/1984 | Smith | 210/755 |
| 4,579,665 | 4/1986 | Davis et al. | 210/764 |
| 4,643,835 | 2/1987 | Koeplin-Gall et al. | 210/764 |
| 4,789,489 | 12/1988 | Hollis et al. | 210/764 |
| 4,816,163 | 3/1989 | Lyons et al. | 210/689 |
| 4,906,385 | 3/1990 | Lyons et al. | 210/749 |

FOREIGN PATENT DOCUMENTS

| | | |
|---|---|---|
| 2642606 | 4/1977 | Fed. Rep. of Germany. |
| 1460037 | 11/1966 | France. |
| 81535 | 8/1974 | Japan. |

OTHER PUBLICATIONS

Ramsey et al; "Effects of Non-Oxidizing Biocides on Adult *Corbiculas Fluminea*"; 10/17/88.
Vellejo et al, Science 119, pp. 420–422 (1965).
McMahon et al, "Impact of European Zebra Mussel Infestation to the Electric Power Industry", Apr. 1990.
Smith et al; "Clams—A Growing Threat to Inplant Water Systems"; 6/14/79.
McMahon et al; "Effects of Two Molluscicides on the Freshwater Macrofouling Bivalve, Dreissena Polymorpha, the Zebra Mussel"—Apr. 1990.

*Primary Examiner*—Stanley Silverman
*Assistant Examiner*—Neil M. McCarthy
*Attorney, Agent, or Firm*—W. C. Mitchell; J. F. DiPrima

[57] ABSTRACT

A method for controlling zebra mussels in aqueous systems comprising treating aqueous systems which contain zebra mussels or which are prone to zebra mussel infestation with an effective amount of a water-soluble dialkyl diallyl quaternary ammonium polymer (polyquat). A preferred polymer is a poly(quaternary ammonium) compound having the recurring structure [DMDAAX$^-$] resulting from the polymerization of monomeric dimethyl diallyl ammonium X$^-$, wherein X$^-$ is any suitable anion.

3 Claims, No Drawings

METHOD FOR CONTROLLING ZEBRA MUSSELS USING DIALKYL DIALLYL AMMONIUM POLYMERS

BACKGROUND OF THE INVENTION

The present invention relates to the control of zebra mussels (*Dreissena polymorpha*) in aqueous systems by utilizing as a molluscicide an effective amount of a water-soluble quaternary dialkyl diallyl ammonium polymer (polyquat).

Zebra mussels recently have been discovered in the Great Lakes. It is believed that these mollusks were carried to North America in the ballast of ships from Europe. Zebra mussels reproduce quickly, and attach to virtually any hard surface in contact with an aqueous system in which they are present. These organisms are particularly troublesome to industrial and municipal users of fresh water, as zebra mussels can quickly foul water intakes and process equipment.

Zebra mussels fall within the class Bivalvia of the phylum Mollusca. They are characterized by threadlike tenacles (byssal threads) which enable them to attach themselves to virtually any hard underwater surface. Since a zebra mussel is particularly adherent to the shell of another zebra mussel, these mollusks tend to "stack up", one upon another, so that they can completely clog intake orifices. Additionally, the threads enable the mussels to affix themselves to a surface which is positioned in any plane relative to horizontal. Thus, unlike other mollusks such as Asian clams (Corbicula), zebra mussels are found on the ceilings, vertical surfaces and floors of under water equipment.

On a daily basis, vast quantities of water are removed from rivers, lakes and streams for potable water use and for use in a variety of industrial processes. The greatest industrial use of water is for cooling purposes, and the greatest nonconsumptive industrial demand for water as a heat transfer medium comes from the steam-electric generating industry. Also, municipalities draw water for public consumption.

Source water supports an abundance of biological life forms, many of which cannot be removed from the water before it is used. While some of these biological life forms may not adversely affect municipal or industrial treatment processes, zebra mussels are biofouling organisms which have become a severe problem in North America in a very short time. These mussels foul intake piping and equipment surfaces in municipal water treatment plants and in industrial water systems.

It is believed that zebra mussels did not become prevalent in Lake Erie until late 1988 or 1989. They are now rapidly spreading into Lake Michigan and into the rivers of the Midwest and Northeast. In a relatively short time, they can reach population densities in excess of 30,000 mussels per square meter. For this reason, zebra mussels can completely shutdown municipal and industrial systems which rely on fresh water infested with zebra mussels. It is believed that zebra mussel fouling will eventually threaten virtually every domestic municipal, utility and industrial user of fresh water that draws its supply from a source which is in fluid communication with the Great Lakes.

Zebra mussel fouling of such equipment as intake piping and steam condensers can be extremely troublesome. Immature or small mussels are easily drawn through intake screens. Once inside a system, they can lodge anywhere. The problem is made worse by the fact that, in the larval state, zebra mussels are carried by flowing water throughout treatment and/or process systems.

Effective methods for controlling zebra mussels in the U.S. are not presently known. In Europe, it is common to utilize dual intake systems, so that one system can be mechanically cleaned while the other is in operation, or to draw source water from depths where the maximum water temperature is too cold (below about 13° C.) for zebra mussels to reproduce.

DESCRIPTION OF KNOWN PRIOR ART

Chemical agents for controlling zebra mussels, including chlorine and other oxidizing agents, have been used. However, chlorine is not desirable for environmental reasons.

U.S. Pat. No. 4,462,914 to Smith discloses the use of polyquats such as dimethyl diallyl ammonium chloride polymers to control Asian clams (Corbicula). However, this patent is silent regarding the efficacy of polyquats as agents to control zebra mussels. Additionally, the instant inventors have found the instant polyquats, particularly dimethyl diallyl ammonium chloride polymers, to be substantially more effective against zebra mussels than they are against Asian clams (Corbicula). Further, the instant inventors have found that the instant polymers tend to make zebra mussels less adherent to hard surfaces by interfering with the ability of their byssal threads to attach to a surface in contact with a treated system. The mechanism by which this inhibition occurs is not understood at the present time.

It is also noteworthy that the instant polymers are widely used in municipal and industrial water treatment. For example, dimethyl diallyl ammonium chloride polymers are added as clarification aids to the water intakes of municipal potable water plants. To the best of the inventors, knowledge, however, such polymers have not been added to control zebra mussel growth or fouling or to reduce the adherence of zebra mussels to underwater surfaces.

Additionally, polyquaternary compounds have been utilized for control of microorganisms such as bacteria, fungi, and algae in aqueous systems. See, e.g., U.S. Pat. Nos. 4,113,709 and 4,111,679. Simple quaternary ammonium compounds have been used to control fouling by microorganisms and molluscs. See, e.g., Nashimura et al., Japan Kokai No. 74 81,535 (1974); Roth, German Offenlegungsschrift No. 2,642,606; Sindery, French Pat. No. 1,460,037 and Vellejo et al., *Science* 119, 420-422 (1954).

Ramsey et al, "Effects of Nonoxidizing Biocides on adult *Corbicula fluminea*" (1988), disclose the use of various biocides, including dodecylguanidine hydrochloride (DGH), benzalkonium chloride, pyridinium chloride, dioctyl dimethyl ammonium chloride, poly-[oxyethylene(dimethylimino)-ethylene (dimethylimino)-ethylene dichloride], glutaraldehyde, 2,2-dibromo-3-nitrilo propionamide, N-4-dihydroxy-$\alpha$-oxobenzene ethanimidoyl chloride, 5-chloro-2-methyl-4-isothiazolin-3-one/2-methyl-4-isothiazolin-3one, N-[($\alpha$)-(1-nitroethyl) benzyl] ethylenediamine and 2-(tert-butylamino)-4-chloro-6(ethylamine)-5-triazine, to control Asian clams.

U.S. Pat. No. 4,816,163, to Lyons et al, discloses the use of water-soluble alkyl guanidine salts, alone or in combination with methylene bis-thiocyanate or alkyl dimethyl benzyl ammonium chloride, to control the biofouling of macroinvertebrates, particularly Corbicula. At column 2, lines 18-20, the '163 patent states that: "Another fresh water mollusk, Dreissna -the zebra mussel, causes fouling problems in Europe to cooling systems in a similar manner as the Asiatic Clam." The inventors note, however, that Asiatic clams do not adhere to hard surfaces, instead remaining in areas where silt deposits are present. Thus, Asiatic clams do not coat underwater vertical or "ceiling" surfaces, as do zebra mussels. Also, Asian clams tend to move around in silt and mud, while zebra mussels are generally sessile once their byssal threads attach, and Corbicula are hermaphroditic, while zebra mussels rely on external fertilization. Due, perhaps, to these or other fundamental distinctions between clams and mussels, the instant polymers have been found to be substantially more effective against zebra mussels than Asiatic clams.

SUMMARY OF THE INVENTION

In accordance with the present invention, there is provided a method for inhibiting the growth of zebra mussels, a method for controlling fouling caused by zebra mussels and a method for reducing the ability of zebra mussels to attach to underwater surfaces. These methods comprise adding an effective amount for the purpose, preferably a molluscicidally effective amount, of a water soluble cationic polymer to an aqueous system which contains zebra mussels and/or zebra mussel larvae. It is also an aspect of the present invention to employ a water soluble polyquaternary ammonium compound (polyquat), preferably a polyquaternary ammonium compound having the recurring structure: [DMDAAX$^-$], wherein DMDAAX$^-$ is monomeric dimethyl diallyl ammonium X$^-$, and wherein X$^-$ is any suitable anion, as the zebra mussel control agent. Co- and terpolymers containing DMDAAX$^-$ units can also be used. The instant invention is particularly effective in municipal potable water treatment plants and in industrial heat exchange/cooling systems, particularly once-through cooling systems.

The instant invention also relates to compositions comprising: (a) an aqueous system containing a plurality of zebra mussels; and (b) at least about 0.1 ppm, on an active basis, of a water soluble dialkyl diallyl quaternary ammonium polymer.

DETAILED DESCRIPTION OF THE INVENTION

The instant invention is directed to a method for controlling the growth of zebra mussels in an aqueous system which contains or is prone to infestation by zebra mussels, comprising adding to such a system an effective amount for the purpose of a water soluble dialkyl diallyl quaternary ammonium polymer (polyquat). These polymers comprise quaternary diallyl dialkyl ammonium moieties wherein the alkyl groups are independently selected from alkyl groups of 1 to 18 carbon atoms, preferably $C_{1-4}$ alkyl, and wherein the counterions are selected from the group consisting of conjugate bases of acids having an ionization constant greater than $10^{-13}$, more preferably selected from the group consisting of fluoride, bromide, chloride, hydroxide, nitrate, acetate, hydrogen sulfate, and primary phosphates, and most preferably chloride. Methyl and ethyl are the preferred alkyl groups, and methyl is most preferred. The most preferred poly(quaternary ammonium) compounds are those having the recurring structure: [DMDAAX$^-$], which represents dimethyl diallyl ammonium X$^-$, wherein the polymer is prepared by polymerizing monomeric dimethyl diallyl ammonium X$^-$ and X$^-$ is any suitable counterion, chloride being most preferred.

As examples of the instant polymers, one may list polydimethyl diallyl ammonium chloride (polyDMDAAC), polydiethyl diallyl ammonium chloride (polyDEDAAC), polydimethyl diallyl ammonium bromide (polyDMDAAB) and polydiethyl diallyl ammonium bromide (polyDEDAAB). PolyDMDAAC's are most preferred.

The molecular weight of the polymer used is not critical. Generally, however, the weight average molecular weight should range between 500 and about 20,000,000, preferably between about 10,000 and about 10,000,000, and most preferably between about 10,000 and about 3,000,000.

The instant polymers may also contain additional moieties. Co- and ter-polymers may be used. For example, polymers containing diethyl diallyl and dimethyl diallyl groups may be used. Additionally, the above dialkyl diallyl quaternary ammonium monomers may be polymerized with any suitable monomer, including but not limited to methacryloyloxyethyl trimethyl ammonium chloride (METAC), methacryloyloxyethyl trimethyl ammonium methosulfate (METAMS), methacrylamido propyl trimethyl ammonium chloride (MAPTAC) acryloyloxyethyl trimethyl ammonium chloride (AETAC), acryloyloxyethyl trimethyl ammonium sulfate (AETAMS) and quaternized derivatives of N, N-dimethyl amino ethyl methacylate, alone or in combination or polymers made by polymerizing any of the above cationic monomers with acylamide, methacylamide or N, N-dimethyl acylamide. For example, DMDAAC/acylyamide, DMDAAC/METAC, METAMS and/or MAPTAC and DMDAAC-/acylamide/METAC, METAMS and/or MAPTAC polymers can be used.

A wide variety of DMDAAC polymers are commercially available from Calgon Corporation, Pittsburgh, PA, and the instant polymers may be prepared using any conventional free radical polymerization technique, such as the technique disclosed by Butler and Angelo, "Journal of American Chemical Society," Vol. 79, p. 3128 (1957) or the technique suggested in U.S. Reissue Pat. No. Re. 28.543. These references are incorporated by reference into this specification.

The expression "controlling the growth of zebra mussels", as used herein, is intended to cover killing, inhibiting the growth of, or preventing the growth of, zebra mussels. In a similar manner, the expression "molluscicidally effective amount" as used herein means an amount which kills, inhibits the growth of, or prevents the growth of zebra mussels in the aqueous systems where the molluscicide is employed.

"Effective amount", as used herein, refers to that amount of polymer necessary to accomplish the purpose of the treatment. The effective amount of water soluble cationic polymer necessary in the methods of the present invention may vary due to such factors as the ambient temperature of the aqueous system being treated, the presence of substances in the water which bind to or otherwise inactivate cationic polymers (for example, silt), the concentration and predominant stage of life cycle of the zebra mussels present in the aqueous system to be controlled, the particular cationic polymer which is employed and other factors. Generally, however, an effective amount will be in the range of from about 0.1 to about 2000 parts per million, preferably about 1 to about 100, and most preferably about 5 to 50 parts per million, based on total weight of active polymer added and the total weight of the water in the aqueous system being treated.

It is noteworthy that aqueous systems oftentimes have a "turbidity demand" for cationic polymers. Thus, cationic polymers interact with and are "tied-up" by solids which cause turbidity. The inventors have found that the portion of cationic polymer "tied-up" by sources of turbidity, such as silt, is ineffective relative to zebra mussels. For this reason, sufficient polymer must be fed to both account for the turbidity demand of the system being treated and to control zebra mussels. A preferred method therefore comprises: (a) determining the turbidity level of the aqueous system to be treated and the corresponding turbidity demand for the particular polymer being fed; (b) feeding sufficient polymer to react with and tie-up the turbidity present, i.e., to account for the turbidity demand of the system by tieing-up existing turbidity; and (c) feeding an effective amount of polymer to control zebra mussels. Preferably, feed steps (b) and (c) can be carried out simultaneously. Step (a) involves routine procedures well within the skill of a water-treatment practitioner.

The inventors also note that veligers, which are free-floating planktonic immature zebra mussels or larva, are produced when water temperatures exceed about 13° C. Peak densities occur between about 20° and 22° C., and temperatures in excess of about 37° C. greatly depress veliger development. In most of the United States, zebra mussel reproduction is seasonal.

Thus between the periods when water temperatures rise to about 13° C. in the spring and fall to below about 13° C. in the autumn, zebra mussels must be treated.

The inventors have found that an 80 $\mu$ (0.08 mm) mesh plankton net can be placed at or near a water intake. By periodically sampling the contents of the net, the presence of zebra mussel veligers can be determined through the use of a stereo microscope. Thus, when veligers are found in the net, polymer treatment can be initiated.

It is believed by the inventors that the instant polyquats react with the gills of zebra mussels to effectively suffocate the mussels, though the inventors do not wish to be bound by this mechanism.

Aside from controlling the growth of zebra mussels, the instant invention further relates to a method for controlling the fouling potential of zebra mussels (biofouling caused by zebra mussels) comprising adding an effective amount of the instant polymers to aqueous systems containing zebra mussels or prone to zebra mussel infestation. Systems prone to zebra mussel infestation include those fresh water systems which are placed in communication with, by any mechanism, a system containing zebra mussels and which are at temperatures between about 13° C. and about 37° C.

Further, the instant invention relates to a method for minimizing the attachment of zebra mussels to hard surfaces, including, but not limited to, pipes, process equipment, boats, walls, rocks, etc., in contact with aqueous systems containing zebra mussels or prone to zebra mussel infestation. The inventors have surprisingly discovered that the instant polymers, through some undefined mechanism, inhibit the ability of zebra mussels to firmly affix themselves to hard underwater surfaces.

The cationic polymers employed in the instant methods can be added to the aqueous system being treated in any conventional manner and at any point best suited to provide ready dissolution and rapid distribution of the polymer to all points in the aqueous system being treated. Feed at the source point is preferred. Various formulations of the cationic polymer which facilitate its dissolution in water may be prepared in accordance with known methods. Any form of the polymer can be used, including but not limited to emulsion, solution or dry forms. Also, other water treatment agents can be added to the system being treated in conjunction with the instant polymers. For example, other biocides, surfactants, scale or corrosion inhibitors, dispersants, flocculants or clarification aids can be used with the instant polymers.

The methods of treatment of the instant invention will be better understood by the following examples, which illustrate the use of a preferred cationic polymer to inhibit the growth of zebra mussels. However, the instant invention should not be construed as being limited in any way by the following examples.

EXAMPLES 1-14

Static Renewal Tests

Various concentrations of poly(dimethyl diallylammonium chloride), DGH and biocide H-700 were established in beakers containing 100 ml of heavily aerated tap water. Ten adult zebra mussels from Lake Erie (*Dreissena polymorpha*), each between 2 mm and 10 mm in shell length, were added to each of the test beakers, as well as to two (2) control beakers containing only heavily aerated tap water. The water was changed daily throughout the test period. Only mussels which were definitely alive (feeding) were used in the test. The zebra mussels were observed daily for signs of life and the results obtained are set forth in the table below.

TABLE 1

| | | STATIC RENEWAL BIOASSAY TEST RESULTS | | | | | |
|---|---|---|---|---|---|---|---|
| Example | | Conc. (mg/L | Number of Organisms Alive | | | | |
| Number | Inhibitor | Prod.) | 0 Hrs. | 24 Hrs. | 48 Hrs. | 72 Hrs. | 96 Hrs. |
| 1* | — | — | 10 | 10 | 10 | 10 | 10 |
| 2* | — | — | 10 | 10 | 10 | 10 | 10 |
| 3 | DGH[1] | 0.75 | 10 | 10 | 10 | 10 | 10 |
| 4 | DGH | 1.5 | 10 | 10 | 10 | 10 | 10 |
| 5 | DGH | 3.0 | 10 | 10 | 10 | 7 | 4 |
| 6 | DGH | 5.0 | 10 | 10 | 10 | 4 | 0 |
| 7 | H-700[2] | 0.75 | 10 | 10 | 10 | 10 | 10 |
| 8 | H-700 | 1.5 | 10 | 10 | 10 | 10 | 10 |
| 9 | H-700 | 3.0 | 10 | 10 | 10 | 10 | 10 |
| 10 | H-700 | 5.0 | 10 | 10 | 10 | 10 | 10 |
| 11 | PolyDMDAAC[3] | 0.75 | 10 | 10 | 10 | 10 | 10 |
| 12 | PolyDMDAAC | 1.5 | 10 | 10 | 10 | 10 | 10 |
| 13 | PolyDMDAAC | 3.0 | 10 | 9 | 9 | 9 | 0 |

TABLE 1-continued
STATIC RENEWAL BIOASSAY TEST RESULTS

| Example Number | Inhibitor | Conc. (mg/L Prod.) | Number of Organisms Alive | | | | |
|---|---|---|---|---|---|---|---|
| | | | 0 Hrs. | 24 Hrs. | 48 Hrs. | 72 Hrs. | 96 Hrs. |
| 14 | PolyDMDAAC | 5.0 | 10 | 7 | 7 | 6 | 0 |
| ORGANISM: | Dreissena polymorpha (Zebra mussel) (10 organisms/conc. 2–10 mm in size) | | | | | | |

*Comparison Examples
[1] DGH is 12.5% active dodecylguanidine hydrochloride, commercially available from Calgon Corporation as H-133A.
[2] H-700 is 25% active (N-[alpha-(1-nitroethyl)benzyl] ethylenediamine, potassium salt, which is commercially available from Calgon Corporation. H-700 has been used to prevent biofilms from adhering to surfaces in contact with aqueous systems.
[3] PolyDMDAAC is a polymer of dimethyldiallyl ammonium chloride (17.5% active) having a weight average molecular weight of about 1,000,000, as determined by gel permeation chromatography, which is commercially available from Calgon Corporation as CatFloc ® DL.

What is claimed is:

1. A method for inhibiting the growth of zebra mussels in an aqueous system which contains zebra mussels or which is prone to the growth of zebra mussels and for inhibiting the ability of said zebra mussels to affix themselves via byssal threads to underwater surfaces comprising adding to said system an effective amount of a water soluble dialkyl diallyl quaternary ammonium polymer.

2. A method for controlling the fouling potential of zebra mussels in an aqueous system which contains zebra mussels or which is prone to the growth of zebra mussels and for inhibiting the ability of said zebra mussels to affix themselves via byssal threads to underwater surfaces comprising adding to said system an effective amount of a water soluble dialkyl diallyl quaternary ammonium polymer.

3. A method for inhibiting the ability of zebra mussels to attach themselves via byssal threads to hard underwater surfaces in contact with an aqueous system containing zebra mussels comprising adding to said aqueous system an effective amount of a water soluble dialkyl diallyl quaternary ammonium polymer.

* * * * *